United States Patent [19]

Pirak et al.

[11] Patent Number: 5,400,771
[45] Date of Patent: Mar. 28, 1995

[54] ENDOTRACHEAL INTUBATION ASSEMBLY AND RELATED METHOD

[76] Inventors: Leon Pirak, 500 Mountain Ave., Springfield, N.J. 07081; Peter J. Wilk, 185 W. End Ave., New York, N.Y. 10023

[21] Appl. No.: 7,056

[22] Filed: Jan. 21, 1993

[51] Int. Cl.⁶ ...................... A61B 1/06; A61M 16/04
[52] U.S. Cl. .................... 128/6; 128/200.26; 128/207.14
[58] Field of Search .............. 128/4, 6, 10, 11, 200.26, 128/207.14, 662.06; 358/98, 105, 107; 348/129, 130, 135, 180

[56] References Cited

U.S. PATENT DOCUMENTS

| | | | |
|---|---|---|---|
| 4,592,343 | 6/1986 | Upsher | 128/11 |
| 4,674,515 | 6/1987 | Andou et al. | 128/6 X |
| 4,742,819 | 10/1988 | George | 128/6 |
| 4,794,911 | 1/1989 | Okada | 128/4 |
| 4,846,153 | 7/1989 | Berci | 128/6 |
| 4,877,016 | 10/1989 | Kantor et al. | 128/6 |
| 4,905,669 | 3/1990 | Bullard et al. | 128/11 |
| 5,188,111 | 2/1993 | Yates et al. | 128/662.06 X |
| 5,261,392 | 11/1993 | Wu | 128/200.26 |
| 5,285,778 | 2/1994 | Mackin | 128/207.14 |

*Primary Examiner*—Richard J. Apley
*Assistant Examiner*—John P. Lenbecker
*Attorney, Agent, or Firm*—R. Neil Sudol; Henry D. Coleman

[57] ABSTRACT

In an endotracheal intubation method, during and after insertion of an endotracheal tube into a trachea of a patient, an image is transmitted along the endotracheal tube from a distal end to a proximal end thereof, thereby enabling an operator to determine proper placement of the endotracheal tube. The image transmitted from the distal end of the endotracheal tube may be automatically monitored by a computer. Upon determination that an incoming image is different from a stored reference image, an alert signal is automatically issued to an operator, thereby indicating that the distal end of the endotracheal tube has moved from a predetermined position within the patient's trachea. A desired image is selected upon insertion of a distal end portion of the endotracheal tube into a patient's trachea.

20 Claims, 2 Drawing Sheets

ENDOTRACHEAL INTUBATION ASSEMBLY AND RELATED METHOD

BACKGROUND OF THE INVENTION

This invention relates to an endotracheal intubation method and an associated instrument assembly for use in performing the method.

During a major surgical operation, a patient is anaesthetized and accordingly requires endotracheal intubation for purposes of providing oxygen to one or both lungs. Generally, unless one of the lungs is being operated on, it is desirable to place the distal end of the endotracheal tube proximally of the junction between the bronchi.

Endotracheal intubation can be difficult even for an experienced anaesthesiologist. The endotracheal tube can be inadvertently placed down the esophagus instead of the windpipe. Moreover, even if the tube is correctly placed at the onset of an operation, it can become dislodged as a consequence of the movements of the patient caused by the operative procedures. Thus, it is important to periodically determine the location of the endotracheal tube during an operation.

The positioning of an endotracheal tube is determined currently by three methods. First, the anaesthesiologist listens to the lungs during a lung oxygenation or pressurization step. The sounds made upon proper endotracheal tube placement are generally different from the sounds made upon an improper placement. Second, the carbon dioxide content of gases expelled via the endotracheal tube is measured. If the tube is improperly placed in the esophagus, there will be no carbon dioxide in the outcoming gases. Third, tissue oxygenation, for example, in the finger, is measured to determine whether the blood is carrying oxygen to the patient's tissues.

None of these methods is universally effective in determining proper endotracheal tube placement.

OBJECTS OF THE INVENTION

An object of the present invention is to provide a method, utilizable during endotracheal intubation, for determining whether an endotracheal tube is properly placed.

Another, more particular, object of the present invention is to provide such a method which is implementable both during intubation and subsequently.

Yet another particular object of the present invention is to provide a method for automatically monitoring endotracheal tube placement during surgery to automatically determine that correcting positioning is maintained.

A further object of the present invention is to provide a device or assembly for carrying out the method of the present invention.

A more specific object of the present invention is to provide such a device or assembly which is at least partially disposable and inexpensive to make.

These and other objects of the present invention will be apparent from the drawings and detailed descriptions herein.

SUMMARY OF THE INVENTION

An endotracheal intubation assembly comprises, in accordance with the present invention, a tubular member provided with openings at a proximal end and a distal end, an illumination transmission guide attached to the tubular member for transmitting optical radiation from the proximal end to the distal end of the tubular member, and an image transmission guide attached to the tubular member for transmitting an image from the distal end to the proximal end of the tubular member.

According to another feature of the present invention, the image transmission guide includes a fiberoptic cable removably attached to the tubular member. More specifically, the fiberoptic cable is removably inserted into an ancillary tube connected to the tubular member, the ancillary tube extending longitudinally therealong from the proximal end to the distal end. The ancillary tube is preferably provided at the distal end with a transparent end cap attached to the ancillary tube in a fluid tight seal.

According to a further feature of the present invention, the endotracheal intubation assembly further comprises an image analyzer operatively connected to the image transmission guide for automatically monitoring the image carried by the image transmission guide. The analyzer preferably includes a comparator for comparing, with a stored image, the image carried by the image transmission guide. A signaling component or alert indicator is operatively connected to the analyzer for indicating to an operator that the distal end of the endotracheal tube has moved from a predetermined position within a patient's trachea.

According to an additional feature of the present invention, the endotracheal intubation assembly also comprises a selector for programming the analyzer to recognize a selected image upon insertion of a distal end portion of the assembly into a patient's trachea. The selector may include a switch or other input device for instructing the analyzer that a currently transmitted image is to be stored as a reference image for comparison with subsequently arriving images.

An endotracheal intubation method comprises, in accordance with the present invention, the steps of (a) inserting an endotracheal tube into a trachea of a patient, (b) transmitting optical radiation along the endotracheal tube from a proximal end to a distal end thereof during the insertion of the endotracheal tube, and (c) transmitting an image along the endotracheal tube from a distal end to a proximal end thereof, thereby enabling an operator to determine proper placement of the endotracheal tube.

Pursuant to another feature of the present invention, the method further comprises the steps of (d) automatically monitoring the image transmitted from the distal end of the endotracheal tube and (e) automatically indicating to an operator that the distal end of the endotracheal tube has moved from a predetermined position within the patient's trachea. The monitoring of the image includes the step of automatically comparing the image with a stored reference image.

Pursuant to yet another feature of the present invention, the method also comprising the steps of (f) selecting a desired image upon insertion of a distal end portion of the endotracheal tube into a patient's trachea and (g) storing the desired image as the reference image.

The method may further comprise the step, performed prior to the insertion of the endotracheal tube into the patient, of inserting an optical fiber bundle into a channel provided on the endotracheal tube, the image being transmitted along the optical fiber bundle. The insertion of the optical fiber bundle into the channel may be stopped upon abutting by a distal end of the optical fiber bundle of a transparent cap at a distal end of the channel.

An endotracheal intubation method comprises, in accordance with a general conceptualization of the present invention, the steps of (i) inserting an endotracheal tube into a trachea of a patient, (ii) during the step of inserting, emitting an energy waveform from a distal end portion of the endotracheal tube in the direction of insertion of the endotracheal tube, (iii) automatically sensing energy waves reflected from internal tissues in the patient upon the step of emitting, (iv) automatically analyzing the sensed reflected waves to determine internal structures of the patient, (v) generating a video image of the internal structures in response to the steps of sensing and analyzing, and (vi) in response to the video image, manipulating the endotracheal tube to position a distal end thereof in a desired location in the trachea of the patient.

An endotracheal intubation method comprises, in accordance with another specific embodiment of the present invention, the steps of (a) inserting an endotracheal tube into a trachea of a patient, (b) emitting ultrasonic pressure waves from a distal end portion of the endotracheal tube in the direction of insertion of the endotracheal tube during the insertion of the tube, (c) automatically sensing ultrasonic waves reflected from internal tissues in the patient, (d) automatically analyzing the sensed ultrasonic waves to determine internal structures of the patient, (e) generating a video image of the internal structures in response to the steps of sensing and analyzing, and (f) in response to the video image, manipulating the endotracheal tube to position a distal end thereof in a desired location in the trachea of the patient.

As discussed hereinabove with reference to a first specific embodiment of the present invention, the steps of emitting and sensing may be implemented via an elongate rod slidably inserted into an ancillary channel on the endotracheal tube, in which case the method further comprises the step of inserting the elongate rod into the ancillary channel prior to the insertion of the endotracheal tube into the trachea of the patient.

As additionally discussed hereinabove with reference to a first specific embodiment of the present invention, the method may also comprise the steps of automatically monitoring the image transmitted from the distal end of the endotracheal tube and automatically indicating to an operator that the distal end of the endotracheal tube has moved from a predetermined position within the patient's trachea. The transmitted image may be automatically compared with a stored reference image which is selected and stored upon insertion of a distal end portion of the endotracheal tube into a patient's trachea.

An endotracheal intubation assembly comprises, in accordance with a general embodiment of the present invention, a tubular member having a proximal end, a distal end, and openings at the proximal end and the distal end, an emitter component disposed at the distal end of the tubular member for emitting an energy waveform from the distal end of the tubular member, a pickup disposed at a distal end of the tubular member for sensing energy waves reflected from internal tissues in the patient, an analyzing component operatively connected to the pickup or sensor for automatically analyzing reflected waves sensed by the pickup to determine internal structures of a patient, and a video unit operatively connected to the analyzing component for generating a video image of the internal structures in response to signals from the analyzing component.

A method in accordance with the present invention is utilizable during endotracheal intubation for determining whether an endotracheal tube is properly placed. The method is easy and essentially foolproof in that the visual identification of internal organs is easier than conventional endotracheal intubation monitoring techniques.

In addition, an instrument assembly and method in accordance with the present invention serve to automatically monitor endotracheal tube placement during surgery to automatically determine that correcting positioning is maintained. The operator (anaesthesiologist) is automatically alerted as to proper tube placement.

Alternatively, the operator can periodically view a video monitor to ascertain that intubation proceeds as planned during the surgery.

DETAILED DESCRIPTION

Figure 1:
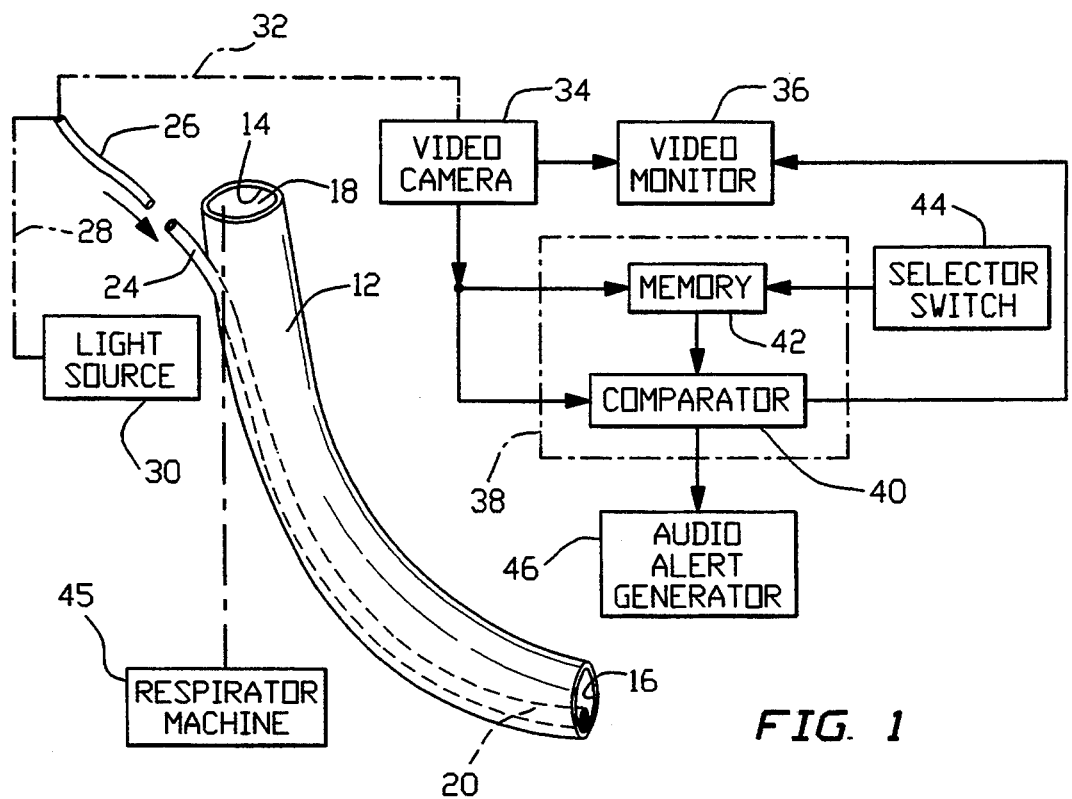
FIG. 1 is partially a schematic perspective view and partially a block diagram of an endotracheal intubation assembly in accordance with the present invention.

As illustrated in FIG. 1, an endotracheal intubation assembly comprises an endotracheal tube or tubular member 12 provided with openings 14 and 16 at a proximal end and a distal end, respectively. Tubular member 12 defines a longitudinally extending lumen (not designated) and is formed along an inner surface 18 with an ancillary tube 20 defining a channel extending parallel to the endotracheal tube lumen.

Figure 2:
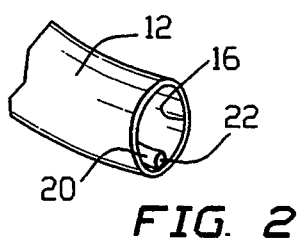
FIG. 2 is a perspective view on a larger scale, of a portion of the endotracheal intubation assembly of FIG. 1.

As illustrated in FIG. 2, tube 20 is provided at a distal end with a transparent end cap 22 which seals the tube. At a proximal end, tube 20 has an inlet stub 24 projecting from tubular member 12 to enable the insertion and subsequent removal of an optical fiber bundle 26. Bundle 26 includes a fiberoptic illumination guide 28 connected to a light source 30 and a fiberoptic cable 32 connected to a video camera 34 in turn connected to a video monitor 36.

Upon insertion of bundle 26 into tube 20 via stub 24, illumination guide 28 conducts electromagnetic radiation from source 30 along tubular member 12. The radiation is emitted through end cap 22 to illuminate internal organic tissues of a patient upon insertion of tubular member 12 through a patient's mouth. An image of the illuminated internal tissues is carried by cable 32 to video camera 34 which displays the image on monitor 36.

During insertion of tubular member 12 into the patient, monitor 36 is watched to ascertain the location of the distal end of the tubular member 12. Tubular member 12 is manipulated from outside the patient to control the positioning of the distal end of the tubular member in response to the image viewed on monitor 36.

As further illustrated in FIG. 1, the endotracheal intubation assembly further comprises a monitoring device 38 (e.g., a computer) connected to camera 34 for receiving images in electrically encoded form therefrom. The encoded images are fed to a comparator component 40 of monitoring device 38 which also receives an encoded video image from a memory 42. The image stored in memory 42 is a reference image selected from the output of camera 34 in response to a signal from a selector switch 44. Selector switch 44 may be a button or sequence of buttons on a computer keyboard (not separately illustrated).

Upon completion of an intubation procedure, an operator activates switch 44 to load a desired image into memory 42 (e.g., an image of the bronchi). The endotracheal tube 12 is connected to a respirator machine 45 so that the tube's lumen communicates with the respirator machine in a closed system. During a subsequent surgical operation, wherein tube 12 is maintained free of obstructions, comparator 40 periodically checks (for example, every twenty seconds) the incoming image from camera 34 against the reference image stored in memory 42 to determine whether the selected intubation position is being maintained. Upon a determination that tubular member 12 has slipped or been dislodged from a selected position, comparator 40 generates an alert signal which causes generation of an alert indication via an audio alert signal generator 46. Alternatively or additionally, the alert signal may be communicated via video monitor 36.

Upon termination of the operation and removal of tubular member 12 from the patient, bundle 26 is extracted from tube 20 via stub 24. Bundle 26 may be reused in a subsequent operation, while tubular member 12 is discarded.

Figure 3:
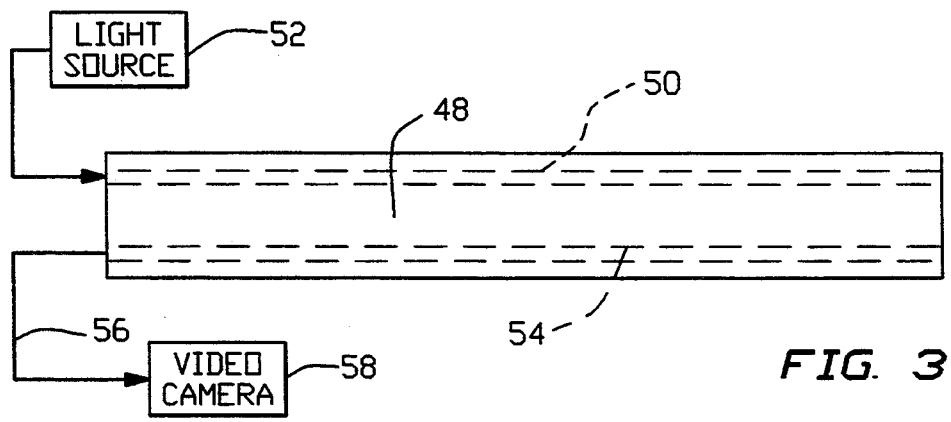
FIG. 3 is partially a schematic side elevational view and partially a block diagram of a modified endotracheal intubation assembly in accordance with the present invention.

As illustrated in FIG. 3, another endotracheal intubation assembly includes an endotracheal tube or tubular member 48 provided with a permanent illumination guide 50 connectable to a light source 52. The endotracheal tube 48 is further provided with a channel 54 for the insertion of a reusable fiberoptic cable 56 extending to a video camera 58. The remainder of the endotracheal intubation assembly of FIG. 3 is the same as the system described hereinabove with reference to FIG. 1.

Figure 4:
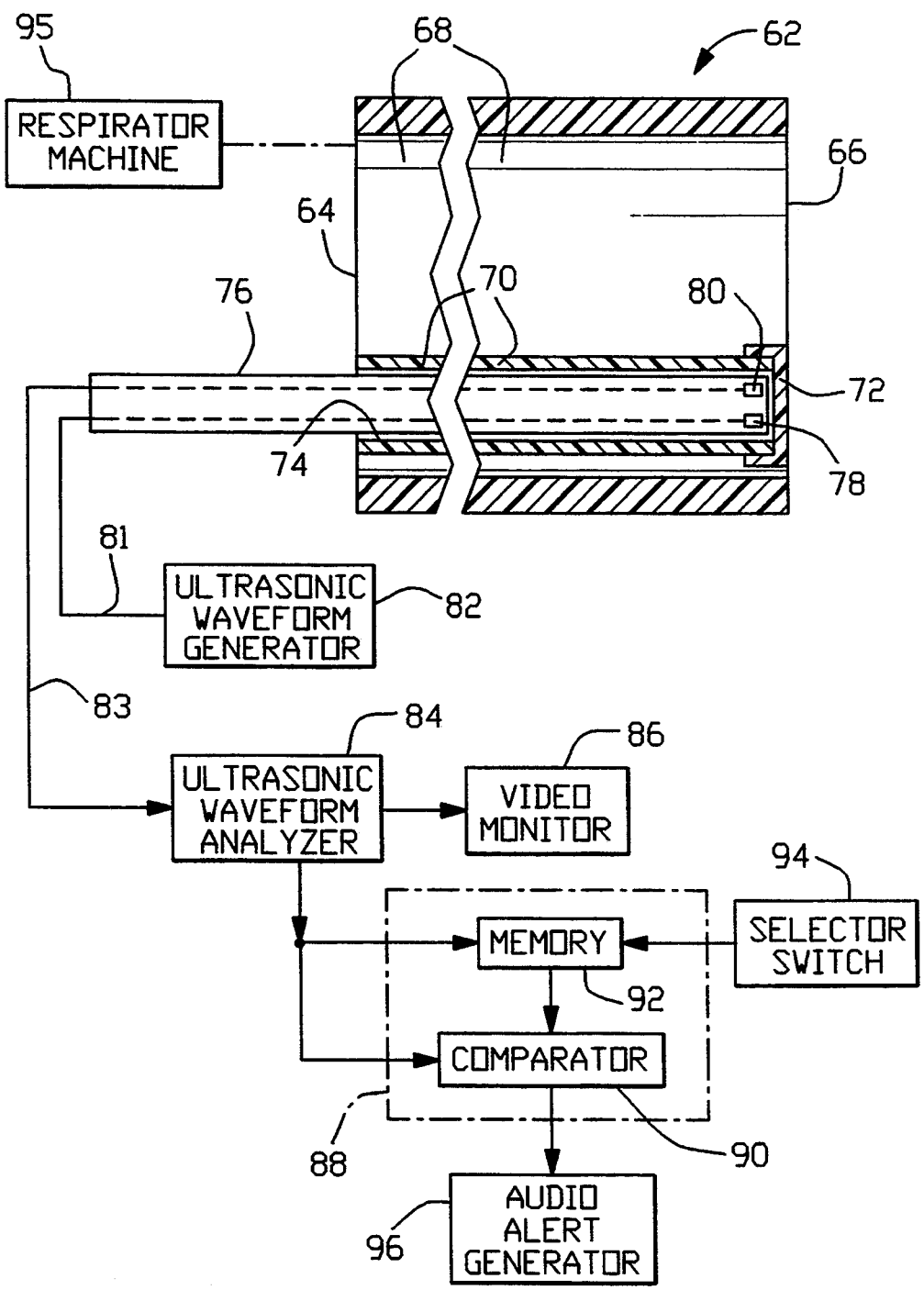
FIG. 4 is partially a partial schematic cross-sectional view, on an enlarged scale, and partially a block diagram of another endotracheal intubation assembly in accordance with the present invention.

As illustrated in FIG. 4, an endotracheal intubation assembly comprises an endotracheal tube or tubular member 62 provided with openings 64 and 66 at a proximal end and a distal end, respectively. An inner surface 68 of tubular member 62 defines a longitudinally extending lumen. An ancillary tube 70 defining a channel extending parallel to the endotracheal tube lumen is attached to tubular member 62 along inner surface 68.

Tube 70 is provided at a distal end with an end cap 72 which seals the tube. At a proximal end, tube 70 has an inlet aperture 74 to enable the insertion and subsequent removal of a flexible rod 76. Rod 76 is provided at a distal end with an electromechanical transducer 78 for emitting ultrasonic pressure waves from the distal end of tubular member 62. In addition, rod 76 is provided at its distal end with an electromechanical transducer 80 for sensing or picking up ultrasonic pressure waves reflected back to the distal end of tubular member 62 from internal structures of a patient during an endotracheal intubation procedure.

Transducer 78 is connected via one or more electrical leads 81 to a source or generator 82 of an ultrasonic frequency electrical signal, while transducer 80 is connected via one or more electrical leads 83 to a computer 84 or other component for analyzing ultrasonic frequencies sensed by pickup transducer 80. Ultrasonic analyzer computer 84 generates a video signal transmitted to a video monitor 86.

Upon insertion of rod 76 into tube 70 via inlet aperture 74 and during insertion of the endotracheal tube into a patient, generator 82 transmits an ultrasonic signal along leads 81 to transducer 78. Transducer 78 consequently emits an energy waveform in the form of an ultrasonic pressure wave from the distal end of tubular member 62. The pressure waveform is emitted through end cap 72 to impinge upon internal organic tissues of a patient upon insertion of tubular member 62 through a patient's mouth. An image of the internal tissues is generated by computer or analyzer 84 and displayed on video monitor 86.

During insertion of tubular member 62 into the patient, monitor 86 is watched to ascertain the location of the distal end of the tubular member 62. Tubular member 62 is manipulated from outside the patient to control the positioning of the distal end of the tubular member in response to the image viewed on monitor 86.

As further illustrated in FIG. 4, the endotracheal intubation assembly further comprises a monitoring device 88 (e.g., another computer or microprocessor) connected to analyzer 84 for receiving images in electrically encoded form therefrom. The encoded images are fed to a comparator component 90 of monitoring device 88 which also receives an encoded video image from a memory 92. The image stored in memory 92 is a reference image selected from the output of analyzer 84 in response to a signal from a selector switch 94. Selector switch 94 may be a button or sequence of buttons on a computer keyboard (not separately illustrated).

Upon completion of an intubation procedure, an operator activates switch 94 to load a desired image into memory 92 (e.g., an image of the bronchi). The endotracheal tube 62 is connected to a respirator machine 95 so that the tube's lumen (68) communicates with the respirator machine in a closed system. During a subsequent surgical operation, wherein tube 62 is maintained free of obstructions, comparator 90 periodically checks (for example, every twenty seconds) the incoming image from analyzer 84 against the reference image stored in memory 92 to determine whether the selected intubation position is being maintained. Upon a determination that tubular member 62 has slipped or been dislodged from a selected position, comparator 90 generates an alert signal which causes generation of an alert indication via an audio alert signal generator 96. Alternatively or additionally, the alert signal may be communicated via video monitor 86.

Upon termination of the operation and removal of tubular member 62 from the patient, rod 76 is extracted from tube 70 via aperture 74. Rod 76 may be reused in a subsequent operation, while tubular member 62 is discarded.

Although the invention has been described in terms of particular embodiments and applications, one of ordinary skill in the art, in light of this teaching, can generate additional embodiments and modifications without departing from the spirit of or exceeding the scope of the claimed invention. For example, a fiberoptic image transmission guide may be permanently attached to an endotracheal tube. However, it is expected that such an assembly would result in elevated costs. In addition, the automatic monitoring may be eliminated to control costs.

In the embodiment of FIG. 4, the information stored in memory 92 and evaluated by comparator 90 may take a form equivalent to a video image. For instance, analyzer 84 may process the incoming reflected ultrasonic waves to produce a structural codification not in the form of a video signal. The selector switch 94 may nevertheless be actuated in conjunction with an image on monitor 86, so that the structural information in memory 92 is correlated to the desired image and corresponding intubation configuration.

Accordingly, it is to be understood that the drawings and descriptions herein are profferred by way of example to facilitate comprehension of the invention and should not be construed to limit the scope thereof.

What is claimed is:

1. An endotracheal intubation method, comprising the steps of:
   inserting an endotracheal tube into a trachea of a patient;
   during said step of inserting, emitting ultrasonic pressure waves from a distal end portion of said endotracheal tube in the direction of insertion of said endotracheal tube;
   automatically sensing ultrasonic waves reflected from internal tissues in the patient;
   automatically analyzing the sensed ultrasonic waves to determine internal structures of said patient;
   generating a video image of said internal structures in response to said steps of sensing and analyzing;
   in response to said video image, manipulating said endotracheal tube to position a distal end thereof in a desired location in the trachea of the patient;
   upon the manipulating of said endotracheal tube to said desired location, storing, as a reference image, a selected image of internal structures of the patient;
   upon the storing of said reference image, automatically comparing said video image with said reference image; and
   upon detecting a difference between said video image and said reference image in said step of comparing, automatically indicating to an operator that said distal end of said endotracheal tube has moved from said desired location.

2. The method defined in claim 1 wherein said steps of emitting and sensing are implemented via an elongate rod slidably inserted into an ancillary channel on said endotracheal tube, further comprising the step of inserting said elongate rod into said ancillary channel prior to the insertion of said endotracheal tube into the trachea of the patient.

3. The method defined in claim 1, further comprising the step of displaying said video image on a video monitor.

4. An endotracheal intubation assembly, comprising:
   a tubular member having a proximal end and a distal end, said tubular member being provided with openings at said proximal end and said distal end;
   emission means disposed at said distal end of said tubular member for emitting an ultrasonic pressure waveform from said distal end of said tubular member;
   pickup means disposed at a distal end of said tubular member for sensing ultrasonic pressure waves reflected from internal tissues in the patient;
   analyzing means operatively connected to said pickup means for automatically analyzing reflected ultrasonic pressure waves sensed by said pickup means to determine internal structures of a patient;
   memory means for storing a reference;
   comparator means operatively connected to said analyzing means and said memory means for automatically comparing a detected internal structure with the stored reference; and
   alert means operatively connected to said comparator means for automatically indicating to an operator that said distal end of said endotracheal tube has moved from a predetermined position within the patient's trachea.

5. An endotracheal intubation assembly, comprising:
   a tubular member having a proximal end and a distal end, said tubular member defining a longitudinally extending lumen having openings at said proximal end and said distal end;
   radiation transmission means attached to said tubular member for transmitting electromagnetic radiation from said proximal end to said distal end of said tubular member along a first path separate from said lumen;
   image transmission means attached to said tubular member for transmitting an image from said distal end to said proximal end of said tubular member along a second path separate from said lumen;
   analyzing means operatively connected to said image transmission means for automatically monitoring image information carried by said image transmission means; and
   alert means operatively connected to said analyzing means for indicating to an operator that said distal end has moved from a predetermined position within a patient's trachea.

6. The assembly defined in claim 5 wherein said ancillary tube is provided at said distal end with a transparent end cap.

7. The assembly defined in claim 6 wherein said end cap is attached to said ancillary tube in a fluid tight seal.

8. The assembly defined in claim 5, further comprising selection means for programming said analyzing means to recognize a selected image upon insertion of a distal end portion of the assembly into a patient's trachea.

9. The assembly defined in claim 5 wherein said analyzing means includes comparator means for comparing, with a selected image, the image carried by said image transmission means.

10. The assembly defined in claim 5 wherein said image transmission means includes a fiberoptic cable removably attached to said tubular member.

11. The assembly defined in claim 10 wherein an ancillary tube is connected to said tubular member and extends longitudinally therealong from said proximal end to said distal end, said fiberoptic cable being removably inserted into said ancillary tube.

12. An endotracheal intubation method, comprising the steps of:
   providing an endotracheal tube having a longitudinally extending lumen and a distal end and a proximal end;
   inserting said endotracheal tube into a trachea of a patient;
   upon placement of said endotracheal tube at a desired position within the patient's trachea, connecting said endotracheal tube to a respirator machine so that said lumen communicates with said respirator machine in a closed system;

upon connection of said respirator machine to said endotracheal tube, performing a surgical operation on the patient;

maintaining said lumen free of obstructions during performance of said operation;

during performance of said operation, transmitting electromagnetic radiation along said endotracheal tube from said proximal end to said distal end thereof;

also during performance of said operation, transmitting, along said endotracheal tube from said distal end to said proximal end thereof, encoded structural information pertaining to internal organic structures of the patient;

upon placement of said endotracheal tube at said desired position within the patient's trachea and prior to the performance of said surgical operation, storing, as reference data in encoded form, selected internal organic structures of the patient at said desired location; and during performance of said operation, monitoring the encoded structural information transmitted from the distal end of said endotracheal tube, to determine whether said distal end of said endotracheal tube has moved from said desired position, said step of monitoring including the step of automatically comparing the transmitted encoded structural information with said reference data.

13. The method defined in claim 12 wherein said step of transmitting includes the step of transmitting a video image along said endotracheal tube from said distal end to said proximal end thereof, said encoded structural information being contained in said video image, said reference data including a reference image, said step of monitoring including the step of comparing said video image with said reference image.

14. The method defined in claim 13 wherein said step of monitoring includes the step of operating a comparator device to compare said video image with said reference image automatically to determine that said distal end of said endotracheal tube has moved from said predetermined position.

15. The method defined in claim 13 further comprising the step, performed prior to said step of inserting, of inserting an optical fiber bundle into a channel provided on said endotracheal tube, said video image being transmitted along said optical fiber bundle.

16. The method defined in claim 13, further comprising the step of displaying said video image on a video monitor.

17. The method defined in claim 15 wherein insertion of said optical fiber bundle into said channel is stopped upon a distal end of said optical fiber bundle abutting a transparent end cap at a distal end of said channel.

18. An endotracheal intubation method, comprising the steps of:

inserting an endotracheal tube into a trachea of a patient;

during said step of inserting, transmitting optical radiation along said endotracheal tube from a proximal end to a distal end thereof;

during said step of inserting, transmitting an image along said endotracheal tube from a distal end to a proximal end thereof, thereby enabling an operator to determine proper placement of said endotracheal tube;

upon placement of said endotracheal tube at a desired position within the patient's trachea, selecting a correlated image of tracheal or bronchial structures of the patient, corresponding to said desired position;

storing said correlated image as a reference image;

also upon placement of said endotracheal tube at said desired position within the patient's trachea, continuing to transmit the image along said endotracheal tube from a distal end to a proximal end thereof; and additionally upon placement of said endotracheal tube at said predetermined position, automatically monitoring the image transmitted from the distal end of said endotracheal tube and automatically indicating to an operator that said distal end of said endotracheal tube has moved from said predetermined position, said step of monitoring including the step of automatically comparing the image transmitted from the distal end of said endotracheal tube with said reference image.

19. An endotracheal intubation method, comprising the steps of:

providing an endotracheal tube having a longitudinally extending lumen and a distal end and a proximal end;

inserting said endotracheal tube into a trachea of a patient;

upon placement of said endotracheal tube at a predetermined position within the patient's trachea, connecting said endotracheal tube to a respirator machine so that said lumen communicates with said respirator machine in a closed system;

upon connection of said respirator machine to said endotracheal tube, performing a surgical operation on the patient;

maintaining said lumen free of obstructions during performance of said operation;

during performance of said operation, emitting ultrasonic pressure waves from a distal end portion of said endotracheal tube in the direction of insertion of said endotracheal tube;

automatically sensing ultrasonic waves reflected from internal tissues in the patient;

automatically analyzing the sensed ultrasonic waves to determine internal structures of the patient;

generating a video image of said internal structures in response to said steps of sensing and analyzing;

upon the placement of said endotracheal tube at said predetermined position and prior to said step of performing said surgical operation, storing, as a reference image, a selected image of internal structures of the patient;

upon the storing of said reference image, automatically monitoring the video image to determine whether said distal end of said endotracheal tube has moved from said predetermined position, said step of monitoring including the step of automatically comparing said video image with said reference image.

20. An endotracheal intubation method, comprising the steps of:

providing an endotracheal tube having a longitudinally extending lumen and a distal end and a proximal end;

inserting said endotracheal tube into a trachea of a patient;

upon placement of said endotracheal tube at a predetermined position within the patient's trachea, connecting said endotracheal tube to a respirator machine so that said lumen communicates with said respirator machine in a closed system;

upon connection of said respirator machine to said endotracheal tube, performing a surgical operation on the patient;

maintaining said lumen free of obstructions during performance of said operation;

during performance of said operation, emitting ultrasonic pressure waves from a distal end portion of said endotracheal tube in the direction of insertion of said endotracheal tube;

automatically sensing ultrasonic waves reflected from internal tissues in the patient;

automatically analyzing the sensed ultrasonic waves to determine an internal structure of the patient;

upon placement of said endotracheal tube at said predetermined position within the patient's trachea and prior to the performance of said surgical operation, storing, as reference data in encoded form, selected internal organic structures of the patient at said predetermined position; and during performance of said operation, automatically comparing the automatically determined internal structure with said reference data to determine whether said distal end of said endotracheal tube has moved from said predetermined position.

* * * * *